(12) United States Patent
Lesniak

(10) Patent No.: US 6,438,255 B1
(45) Date of Patent: Aug. 20, 2002

(54) TRANSIENT THERMAL MARKING OF OBJECTS

(75) Inventor: Jon R. Lesniak, Madison, WI (US)

(73) Assignee: Stress Photonics, Inc., Madison, WI (US)

(*) Notice: Subject to any disclaimer, the term of this patent is extended or adjusted under 35 U.S.C. 154(b) by 0 days.

(21) Appl. No.: 09/549,376

(22) Filed: Apr. 14, 2000

(51) Int. Cl.⁷ ................................................ G06K 9/00
(52) U.S. Cl. ...................................................... 382/107
(58) Field of Search .............................. 382/107, 118, 382/128, 181; 250/316.1, 318; 356/51

(56) References Cited

U.S. PATENT DOCUMENTS

| | | | |
|---|---|---|---|
| 3,592,545 A | 7/1971 | Paine | 356/32 |
| 4,741,621 A | 5/1988 | Taft et al. | 356/606 |
| 4,842,413 A | 6/1989 | Kuijpers et al. | 356/426 |
| 4,920,385 A | 4/1990 | Clarke et al. | 356/237.2 |
| 4,983,836 A * | 1/1991 | Matoba et al. | 250/330 |
| 4,996,426 A | 2/1991 | Cielo et al. | 250/330 |
| 5,066,019 A * | 11/1991 | Dean et al. | 273/348.1 |
| H999 H | 12/1991 | Merkel et al. | 356/239.1 |
| 5,074,661 A | 12/1991 | Reynolds et al. | 356/237.2 |
| 5,085,516 A | 2/1992 | Bertrand et al. | 356/394 |
| 5,239,178 A | 8/1993 | Derndinger et al. | 250/234 |
| 5,432,595 A | 7/1995 | Pechersky | 356/35.5 |
| 5,683,181 A | 11/1997 | Shepard | 374/165 |
| 5,737,074 A | 4/1998 | Haga et al. | 356/237.2 |
| 5,760,891 A | 6/1998 | Graff | 356/237.2 |
| 5,775,806 A * | 7/1998 | Allred | 374/124 |
| 5,847,390 A * | 12/1998 | Long et al. | 250/332 |
| 5,911,001 A | 6/1999 | Kawada | 382/141 |
| 6,277,082 B1 * | 8/2001 | Gambale | 600/549 |
| 6,366,802 B1 * | 4/2002 | Haber et al. | 600/474 |

OTHER PUBLICATIONS

"Cinefex 72 . . . the journal of cinematic illusions—Titanic" –Dec. 1997 –p. 40.

* cited by examiner

*Primary Examiner*—Andrew W. Johns
*Assistant Examiner*—Shervin Nakhjavan
(74) *Attorney, Agent, or Firm*—Lathrop & Clark LLP

(57) ABSTRACT

Portions of an organism, object, engineering structure, sheet or moving web are selectively heated, and thereby marked with a thermal spot or spots, which are imaged by an infrared camera. The positions of the imaged markings are tracked over time, to thereby extract kinematic and other information about the marked object.

18 Claims, 3 Drawing Sheets

TRANSIENT THERMAL MARKING OF OBJECTS

BACKGROUND OF THE INVENTION

The present invention relates to process control utilizing optical markings in general and to optical markings used to detect displacement in particular.

In many experimental and industrial processes, imaging of marks placed on an object are used to detect displacement of the object or portions thereof. Determination of displacement between two marks on an object can be used to determine strain, vibrational displacement, orientation, bending, and displacement and its derivatives: velocity and acceleration.

Marking an object generally involves painting or attaching visible marks to the object. In manufacture, the marks may add expense both in applying and removing. Further, some products such as paper are rendered useless by marking. Moreover, in experimental applications it can be difficult to accurately apply marks in a regular pattern. In some experimental situations the markings may themselves interfere with the experiment, particularly with biological systems.

In many manufacturing processes a web or sheet of material is handled and processed through multiple steps. Oftentimes the web or sheet is oriented, distorted, bent, formed, or cut at each step. Process control of the often rapidly moving sheet can demand that witness marks be painted on the sheet being processed to allow high speed imaging of the sheet to detect motion, orientation and plastic or elastic strain in the sheet.

Examples of processes where monitoring a rapidly moving web of material is important are papermaking and secondary papermaking process steps such as coating and slitting the paper. Because paper is featureless, markings must be placed on the web if process controls utilizing image processing are to be used. Many techniques are now available for integrating controls with computer imaging systems, but such systems require visually distinct marks on the object being imaged. Marking paper, however, destroys its economic value.

What is needed is a method of marking an organism, object, web or sheet of material which is only temporary in nature but which allows the marks to be readily imaged

SUMMARY OF THE INVENTION

The method of this invention involves selectively heating portions of a biological organism, object, structure, sheet or moving web with, for example infrared radiation, thereby locally heating and marking the object with a thermal spot. The thermal spot is detectable by an infrared camera and allows tracking the motion of the heated spot over time and extracting kinematic information about the marked object. This technique is most effective with materials which have low thermal conductivity and high emissivity. But most objects have an emissivity and thermal conductivity which allows persistence of a mark for a useful period of time. A paper web is an example of a material where a temperature rise of a few degrees will typically remain visible for many seconds to a minute. A thermal camera can detect a fraction of a decree temperature difference and, for temperatures near room temperature, cooling by radiation dissipates energy relatively slowly. For paper manufacture or processing, the paper web is often processed at 50 to 100 feet per second, so a thermal mark made on the paper's surface will persist for many hundreds of feet.

The simplest marking is a witness mark which allows a clocking of web speed throughout a set of processes. Two marks allow strain to be detected. More complicated patterns include a grid of dots or lines which would allow complete determination of strain in the web.

Grid lines also allow precise determination of orientation between two manufacturing stations which interact with an object. The sheet or object can be marked when the sheet is in a known orientation so that a correlation between the pattern marked by the thermal image and the object is known, or a grid can be written/projected onto an object when its orientation is unknown and its orientation can be determined later when the object is in a known reference frame.

A grid of lines or other regular pattern of lines or circles can be used to form moire patterns between a first image and a second image in which the original image is displaced or rotated. Extreme precision is possible utilizing moire techniques.

In plane vibration can be monitored on structures by tracking motion of thermal spots. Three dimensional information can be obtained by utilizing two or more thermal imaging devices to obtain stereo images. For monitoring vibrational scale movements sub-pixel level changes must be detected. Detection of sub-pixel image shifting is facilitated by knowledge of the thermal gradient along the edges of the thermal spot being detected. This determination of thermal gradient can be by correct observation with a thermal imaging device or with greater sensitivity and simplicity the image may be artificially dithered by motion of an optical element at a known frequency. Analysis of the image data then produces a value for thermal gradient which can be used to detect sub-pixel motion of the image of a thermal spot.

Biomechanical data can be gathered by placing thermal marks on a living person or organ and monitoring displacement of muscles, limbs, joints. Many biological systems are essentially elastic membranes. Three dimensional imaging of the motion of such biological membranes is possible by imaging thermal spots with two or more thermal imaging devices.

It is an object of the present invention to provide a method of temporarily marking objects.

It is another object of the present invention to facilitate process control of moving webs of material.

It is a further object of the present invention to allow the orientation of an object to be determined by computer imaging techniques without permanently marking the object.

It is a yet another object of the present invention to provide a method of determining bending, stretching, or deformation of an object without permanently marking the object.

It is a yet further object of the present invention to provide a method of temporarily marking selected areas of an object for later processing.

It is a still further object of the present invention to provide a method of detecting very small motion of thermal spots by determining the thermal gradient at the periphery of said thermal spots.

It is still another object of the present invention to provide a method of imaging elastic membrane motion in three dimensions.

Further objects, features and advantages of the invention will be apparent from the following detailed description when taken in conjunction with the accompanying drawings.

DESCRIPTION OF THE PREFERRED EMBODIMENTS

Figure 1:
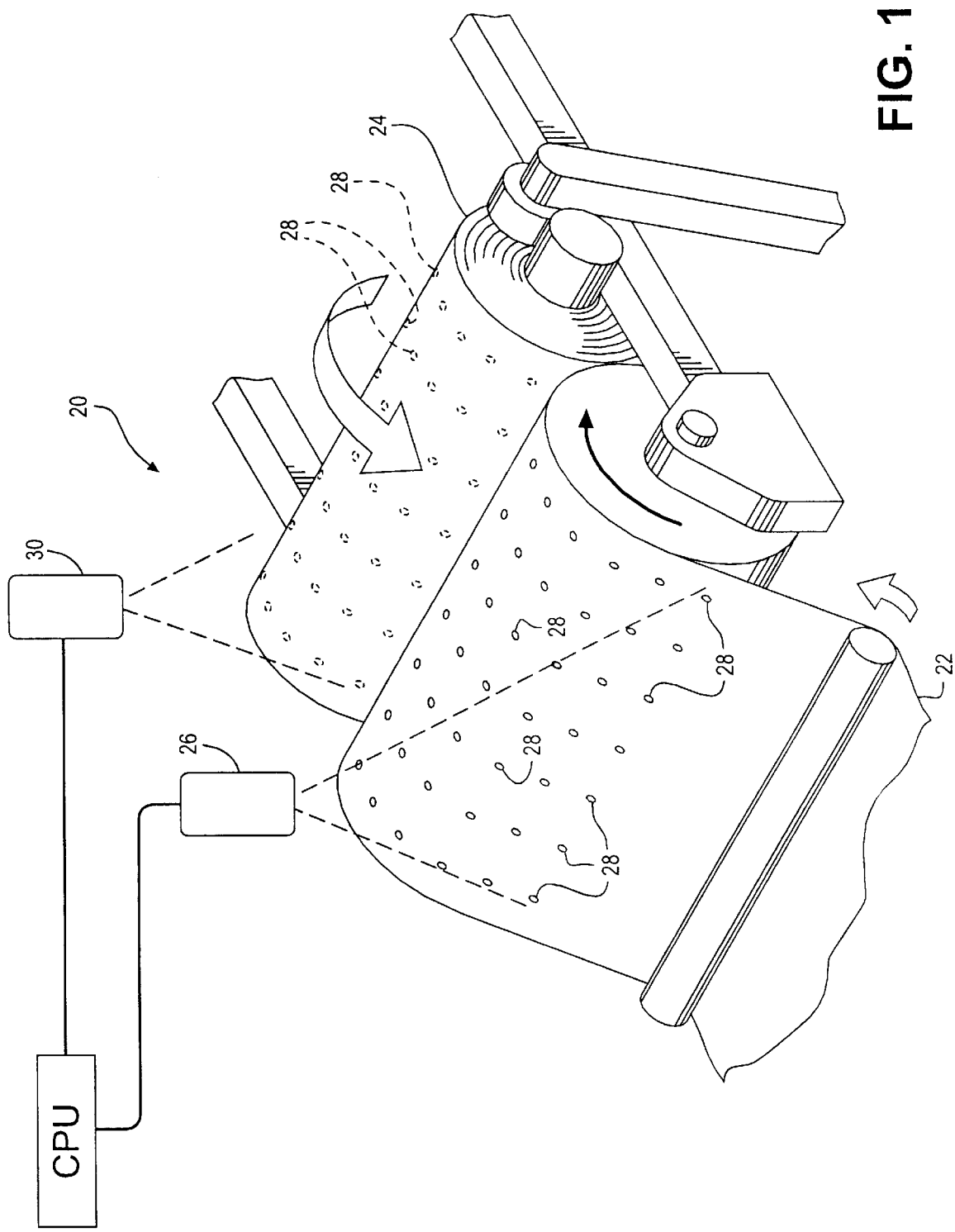
FIG. 1 is pictorial isometric view of the method of this invention being used for marking a paper web on paper winder.
Figure 2:
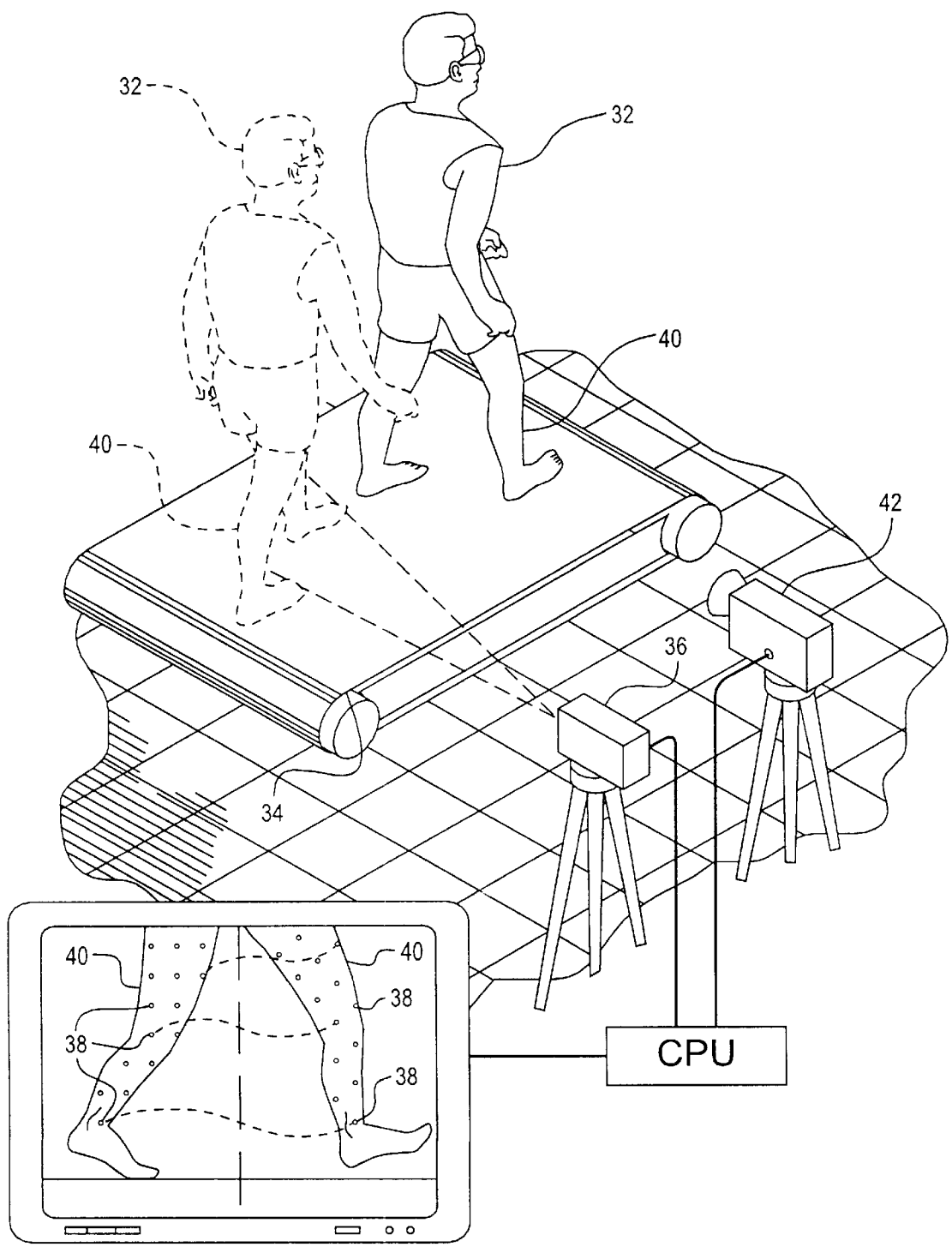
FIG. 2 is a pictorial isometric view of the method of this invention being used to monitor a person undergoing exercise.
Figure 3:
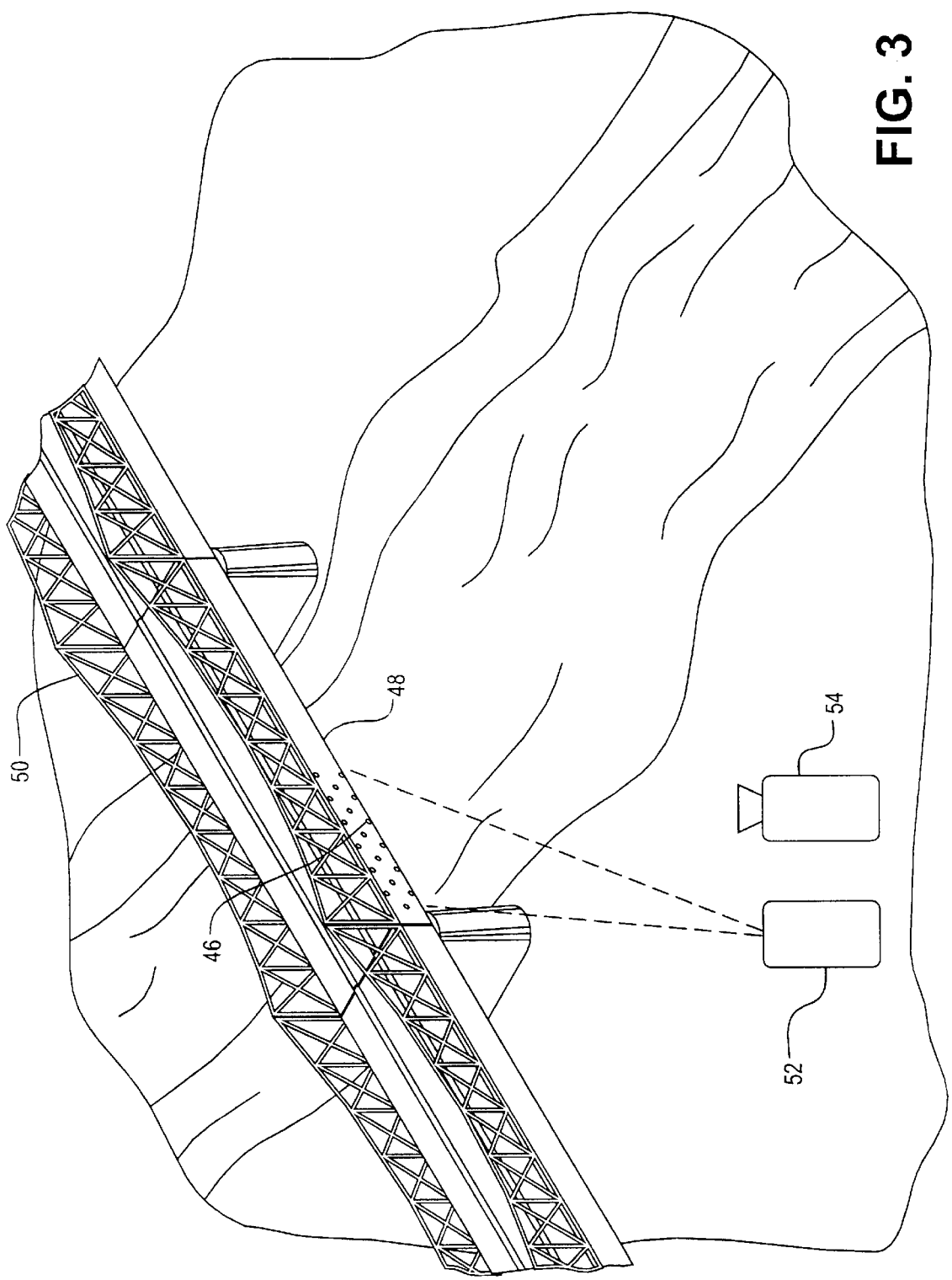
FIG. 3 is a pictorial isometric view of the method of this invention being used to detect in-plane deflections in the structure of a bridge.

Referring more particularly to FIGS. 1–3, wherein like numbers refer to similar parts, examples of the application of the process of this invention in a variety of situations are shown.

The thermal properties of common materials and organisms generally have sufficiently low heat transfer rates to the environment which is at approximately the same temperature so that a object which is marked by having a small region externally heated will retain its elevated temperature for a measurable duration, making possible sequential observations of the marked region over a period of time. At the same time most objects are not so sensitive to minor temperature changes as to be permanently altered by the marking. Hence, by using infrared radiation as a marker, objects which it is undesirable or impractical to permanently mark visually, may be readily and economically marked over a useful duration of the observation without leaving any persistent mark or blemish. Computer-aided image processing techniques may also be used in conjunction with sequential infrared images to extract detailed information about the motion of the object, including speed, acceleration, stress, strain, and displacement of the object as a whole, and of selected portions of the object with respect to the whole.

Several examples of the application of this process are set out below, indicating generally its use in observing moving structures, moving organisms, and static structures under varying loading conditions. Numerous other uses for this method will be readily apparent.

The process of this invention is readily employed to determine the fluctuating conditions of a moving web, such as on a paper winder 20, as shown in FIG. 1. In the winder 20, a web of paper 22 being discharged from a papermaking machine is wound onto a reel 24. Before the paper web 22 is wrapped onto the reel, a projector 26, such as an infrared laser, writes an array of heated dots 28 on the web 22. At some later time when the web has moved a distance from the position at which the dots 28 are written, the web 22 is viewed in the infrared with a camera 30. The infrared camera 30 creates an image of the web 22 from which the dots 28 are detected and their relative locations are calculated a computer or CPU.

The spacing between dots 28 is compared with the known original spacing as written, to detect strain. In FIG. 1 the dots 28 are shown being written onto the top surface of the paper web 22 for simplicity of illustration, but could be written from below the web surface, allowing the heated dots 28 to be viewed directly when the web is wrapped on the reel 24. The dots 28 will be written in a predetermined array or their position may be imaged as they are written.

The output from the camera 30 may alternatively be processed to form a constant image of dots utilizing a stroboscopic effect in which the web is imaged in sequence with the period of the writing of the dots so the pattern remains motionless while varying strains within the web cause the individual dots to move with respect to the overall pattern. Thus by monitoring changing strain in the web it would be possible to use a feedback system to control web tension to maintain web tension constant or to change web tension according to a program sequence.

Paper has an emissivity which is relatively high, around 0.7, and is relatively non-conductive thermally. This means that heat can leave the paper web principally through conduction to a boundary layer of air traveling with the web, and through radiation. At temperatures near room temperature, radiation is relatively inefficient, such that a temperature differential will persist for many seconds up to about one minute. Further, because much is known about the original location of the dots, and changes in strain are likely to be gradual, signal processing, particularly use of a lock-in-algorithm, should allow very small temperature differences to be detected, perhaps as low as a few hundredths of a degree centigrade.

Moire patterns are visual interference patterns which result when a regular array of lines, dots, or circles is overlain with an identical or a different array pattern so that relative motion between the two arrays produces light and dark interference fringes. These light and dark fringes move rapidly with small changes in relative position between the array and its overlay. Moire patterns thus provide a sensitive measure of motion between the arrays. Use of a moire pattern written onto the paper web by the projector 26 and thus provides a visual and analytical aid in detecting small motions between the arrays or portions thereof which are indicative of strain or changing velocity of the web 22.

A moire pattern can be created by projecting a second standard pattern onto the web after the first pattern has undergone strain causing motion between the dots 28. Thus moire pattern is created as the first pattern changes with respect to a fixed second pattern. The second pattern may simply be a virtual pattern within the CPU to make the changes visible when the image pattern and the virtual pattern are displayed together.

This same technique, that of writing a pattern, preferably one suitable for forming moire patterns, onto an object can be used to precisely align a product between manufacturing stages. The infrared pattern leaves no permanent mark, and will not interfere with later processing. If increased duration is required, the infrared pattern can be rewriting forming a new pattern, or duration can be increased by detecting the diminished intensity infrared spots, and directing the infrared laser to reheat the spots where they are currently located. Where a new pattern is written, a correlation between the old and new patterns can be obtained before the old pattern fades to invisibility. Such linked correlation between patterns means that the thermal pattern is essentially continuous because of the positional correlation between sequential thermal patterns.

As an object moves, it is possible for one thermal spot to move across another, thus confusing a computerized tracking of motion based on tracking specific thermal spots. This is a major problem where digital image capture of human motion is attempted. Existing techniques utilize infrared retro-reflectors illuminated by infrared light. Three dimensional computer tracking of the infrared retro-reflectors is confused where reflectors pass in front of other reflectors.

Where thermal patterns are continually rewritten, the pattern of dots can be adjusted so super-positioning is avoided, while simultaneously correlation of individual dots over time is maintained by relating each new thermal pattern to previous thermal patterns, such correlation not necessarily being on a one spot to one spot basis, but between each element of the new pattern and the entire old pattern.

An additional use of infrared written marks is as a guide to a computer driven tool such as a printer, router, knife or taping device. In many natural products it is necessary to properly orient the object before additional process steps can be taken. However the station, equipment, or jig necessary for orientation may not be suitable for performing later operations. In some cases a first operation may involve signal processing as wherein the condition or location of a feature is first determined, followed by a step which applies a tool, process, or material along a tool path defined in relation to the feature identified in the first operation. Oftentimes any normal marking will impede the later operation or leave a residual mark which, for functional or aesthetic reasons, is undesirable.

According to the process of the present invention, the workpiece may be marked with infrared illumination, and then imaged with an infrared camera to continuously or intermittently determine the position of the marks. This positioning information may then be fed to a controller for a machine which operates on the workpiece.

Engineering and scientific experimentation will often require tracking movement on a biological system, however any such marking may interfere with the system being observed. For example, in tracking the movement of a human subject, as shown in FIG. 2, motion data may be collected from a person 32 walking on a treadmill 34. A projector 36, such as an infrared laser, writes identification marks 38 onto the subject's leg 40 when the subject is in a first position. An infrared camera 42 is directed at the subject, and allows imaging of the marks 38 as the person 32 walks in place on the treadmill 34. A first image of the marks on the person is captured by the infrared camera, and preserved for later comparison, then after a selected period of time a second image of the marks on the person is captured and compared to the first image. Multiple images may be collected to develop a time-dependent history of position as well as strain between the marks 38 over time. A display 44 shows the displacement of the marks 38 between the two instances in time. Derivatives of the time-dependent history of position/displacement allow determination of velocities and acceleration from which forces applied can be derived.

Marking a human subject with material tags, greasepaint, or ink, can be time consuming and may be objected to by the subject. Furthermore, to obtain the data desired, it may be necessary to precisely place marks in positions which can only be determined by tracking marks and repositioning them until data characteristic of a particular phenomenon or diagnostic test is obtained. Many studies concerning human or animal motion might benefit from many test subjects such that automatic, non-invasive and rapid marking, using the process of this invention, will greatly facilitate collecting data.

Beyond using a live subject, information about range of motion, stretching of individual muscles, and tendons can be determined by utilizing a cadaver limb. Such data could be obtained by placing thermal markings on individual muscles and tendons. Normal methods of marking objects are difficult to employ on tissue, and the marks can interfere with the motion of the tissue. Further, with most experimental systems the placement of the marks may require considerable trial and error before useful data is obtained. With the method of this invention, should it be desired to reposition the marks, the experimenter need only wait a minute or so for the heat applied to the marked regions to dissipate, and then immediately mark the specimen in a new fashion. Again it may be desirable to employ a computerized search routine which will move the markers during each refresh cycle until certain conditions are met.

Marking of organs within a living patient undergoing surgery could be used to facilitate computer aided navigation and placement of equipment within, for example, the abdominal cavity.

Therapeutic radiation is typically delivered by a computer positioned source, which may be optically aligned with marking on the patient's body. A less invasive technique could use thermal marks, and allow automatic tracking of patient movements during dose delivery.

Thermal marking may be useful even where the persistence of the mark is only a fraction of a second because the mark can be periodically renewed. Periodic renewal could take the form of constantly placing the same array of marks onto an object and imaging the refreshed marks against the previous marks which are fading, or the mark could be tracked and targeted for refreshing.

Plants are another type of specimen which may benefit from thermal marking. Plants may be even more sensitive to conventional marking techniques because of the interference with photosynthesis which conventional marking techniques may produce. Thermal marking, on the other hand, avoids this problem and thus may be usefully analyzed for motion and strains in the leaves and stems of plants.

Another feature of thermal marking which may have many practical advantages is that the brightness of an illuminated surface at a fixed detector remains constant with increasing distance, although the size of the detected region will decrease. Thus, so long as the thermal mark is sufficiently large to illuminate a single sensor in a sensor array, detectability will not decrease with distance. Moreover, by using an infrared laser to create the thermal marks, the marking can be accomplished at great distances.

Long distance marking would allow analysis of engineering structures. Engineering structures are defined to include structures from several tens of feet to thousands of feet long such as bridges, tanks, cranes, ships and similar large structures to be marked. The method of this invention will permit the dynamic analysis of short lived loads such as vibration. Projecting a moire forming pattern 46 onto a structural member 48 of a bridge 50 could allow in-plane vibration to be detected. Typically range finding type sensors/interferometers can only readily measure out of plane vibrations.

As shown in FIG. 3, a high powered infrared laser 52, for example a carbon dioxide laser at 10.6 microns, is directed onto the engineering structure, such as a bridge 50, and writes a pattern 46 which is imaged by a fixed camera 54. As the bridge 50 deflects due to traffic or wind loads the displacement of the bridge can be determined by imaging the pattern 46 and comparing it to the undeflected pattern. This comparison can be accomplished by creating a moire pattern by superimposed the undeflected image on the deflected image.

The deflections due to vibration in a structure typically will be small, such that detection of thermal image motion amounting to a small fraction of a pixel will be necessary. Detection of motion as small as one thousandth of a pixel or smaller may be feasible and desirable. A knowledge of the sharpness of the edge of the thermal dot being imaged allows better detection of small sub-pixel motion. Edge sharpness corresponds to the thermal gradient around the periphery of a thermal dot. This thermal gradient can be directly detected and calculated by imaging a thermal dot. However this may prove difficult and impractical because of the small size of the dot and dot periphery image.

A simple method for determining thermal gradient about a thermal dot is to introduce a small oscillatory motion to the dot image on the image plane, typically by inserting optical elements which cause the image to move back and forth at a selected frequency, for example thirty Hz. The motion of the image at a known frequency and sub-pixel amplitude can be used to calibrate/determine thermal gradient. Because the motion is at a known frequency a lock-in algorithm can readily detect the changes due to the induced oscillatory motion, thus accurately determining thermal gradient. By comparing lock-in determined amplitude with non-lock-in frequency and amplitude determinations, calibration of the detectability of sub-pixel motion will be facilitated.

Detection of vibrational frequency can be with the aid of a reference such as an accelerometer placed on the structure. Alternatively, frequencies can be stepped through, performing a lock-in on a series of selected frequencies, thus performing a search for a frequency containing substantial signal. A fast Fourier transform can also be used to identify frequencies on which to perform lock-in and further data gathering. The use of a digital lock-in filter, explained more extensively in my prior patent, U.S. Pat. No. 5,201,582, the disclosure of which is incorporated by reference herein, may be thought of as simply a digital filter which filters out the portion of the output of the sensor array which does not vary in time with the selected periodicity.

Although many bridges and other engineering structures are constructed of metal, the paint upon the metal surface provides reduced conductivity which should increase persistence of the thermal marks.

The temperature to which selected areas of an object or organism/biological specimen are heated in the process of this invention is variable, and depends on how long the thermal pattern is required to persist, the sensitivity of the detecting apparatus, and whether a lock-in algorithm can be employed. Typically, the object will be raised to a temperature slightly above ambient, i.e., a range from about a hundredth of a degree centigrade up to about 10° C.

A single thermal imaging device detects motion only in a single image plane, however, two or more thermal imaging devices allow for three dimensional determination of each thermal dot's position and motion in three dimensions. For many structures, three dimensional vibration data is desirable. For other systems, it is motion or deformation in three dimensions which is desirable.

Deformable membranes such as organs, for example the heart, are best understood by observing three dimensional motion of the organ.

Digital capture of the motion of people employed in the film industry typically employs multiple cameras capturing 60 to 120 images per second. To achieve such motion capture utilizing thermal dot tracking technology would be expected to similarly involve multiple cameras and high frame rate data acquisition. High speed mechanical systems would of course require even higher rates of data capture particularly where higher frequency modal data is desired.

It should be understood that thermal imaging, or forming a thermal image, refers to the process of capturing an image of an object at a wavelength wherein the thermal emittance of objects dominates. In other words the brightness of objects is dependent on their temperature and emissivity and not principally on reflected light.

It should be understand that a moire pattern may be used to detect in plane motion by repeatedly writing the same thermal pattern on to a object which is undergoing motion or internal strain, this will produce a interference pattern indicative of the motion or strain. Alternatively a single thermal pattern placed on a object may be compared with a virtue image or with a image previously captured.

Moire pattern can be created by superimposed patterns consist of lines circles and various patterns especially created to develop constructive and destructive fringes when one pattern is shifted with respect to a second pattern.

It should be understood that if thermal marking of highly conductive materials like aluminum are necessary, the surface of the object could be painted with a ceramic paint or covered with tape to improve the material's ability to retain a thermal mark.

It is understood that the invention is not limited to the particular construction and arrangement of parts herein illustrated and described, but embraces such modified forms thereof as come within the scope of the following claims.

I claim:

1. A method of analyzing the kinematics of a object by temporarily marking an object comprising:

marking the object by increasing the temperature of selected areas of the object from about 0.01° C. to about 10° C. above ambient to form a selected pattern upon the object;

waiting a selected period of time after marking the object;

forming a thermal image of the object, and detecting the selected pattern upon the object within the image;

comparing the detected selected pattern with the marked selected pattern and detecting an attribute of the object selected from the group consisting of: displacement, derivatives of displacement, orientation, distortion, strain, or bending.

2. A method of analyzing the kinematics of a object by temporarily marking an object comprising:

marking the object by increasing the temperature of selected areas of the object slightly above ambient to form a regular, selected pattern upon the object;

forming a first thermal image of the object, and detecting the regular selected pattern upon the object;

waiting a selected period of time from 0.0 to 10 seconds after marking the object and forming a second thermal image of the object; and comparing the first thermal image with the second thermal image and detecting an attribute of the object selected from the group consisting of: displacement, derivatives of displacement, orientation, distortion, strain, or bending.

3. The method of claim 2 wherein the regular selected pattern is of the type used to form moire patterns and the step of comparing the first thermal image with the second thermal image comprises forming a Moire pattern.

4. A method of monitoring motion of a person comprising the steps of:

warming a plurality of individual selected portions of the body above the temperature of surrounding tissue;

forming a first thermal image of the human person and detecting the individual selected portions;

waiting a period of time, and forming a second thermal image of the human person and again detecting the individual selected portions; and determining the motion of the individually selected portions during the period of time.

5. The method of claim 4 further comprising:

accumulating a multiplicity of thermal images subsequent to the second thermal image, each of said multiplicity of images being separated by a period of time;

detecting in each thermal image the individual selected portions; and determining with respect to each individually selected portion a time-dependent history of position, velocity, and acceleration.

6. The method of claim 5 further comprising the step of determining the strain between each of said individually selected portions in the second and subsequent thermal images with respect to the first thermal image.

7. A method of processing an object comprising the steps of:

selectively heating portions of the object to form an array of selectively heated portions of the object;

forming a thermal image of the object and detecting the array of selectively heated portions; and determining a tool path referenced to the array of selectively heated portions, and moving a tool along the tool path.

8. The method of claim 7 further including the steps of repeatedly forming thermal images of the object to repeatedly detect the selectively heating portions as the tool moves along the tool path, and to repositioning the tool path to remain referenced to the array of selectively heated portions.

9. A method of detecting motion and strain on a biological specimen comprising:

selectively heating a plurality of portions of the biological specimen up to about 10° C. above an ambient temperature of the biological specimen;

forming a sequence of thermal images separated in time which detect the plurality of portions of the biological specimen;

determining the time varying position of each of said plurality of portions of the biological specimen.

10. The method of claim 9 wherein the step of forming a thermal image is accomplished using a camera with maximal sensitivity to the emissivity of a black body at about room temperature.

11. A method of measuring in plane deflections in an engineering structure comprising:

heating a selected region of the engineering structure with a laser to a temperature about several degrees above ambient;

forming a multiplicity of thermal images of at least a portion of the engineering structure including the selected region, each thermal image being formed sequentially in time;

processing the multiplicity of thermal images and extracting information about the motion of the selected region.

12. The method of claim 11 further comprising the step of determining derivatives of position with respect to time of the selected region.

13. The method of claim 11 wherein the step of heating a selected region includes heating a multiplicity of regions to for an array suitable for forming a moire pattern, and wherein the step of processing includes comparing the imaged multiplicity of regions with a fixed array to detect in plane displacement of the engineering structure.

14. The method of claim 11 wherein the laser is a carbon dioxide laser emits light having a wavelength of 10.6 microns.

15. A method of analyzing vibrational motion of portions of an object, comprising the steps of:

marking the object by increasing the temperature of a selected area of the object above ambient, the selected area defining a periphery;

determining the thermal gradient of the periphery of the selected area; and forming a thermal image of the object on a detector image plane, the detector comprising a multiplicity of sensors forming an array, and detecting movement of the image of the selected area upon the object within the image by repeated capture of imaging data followed by signal processing employing the known peripheral thermal gradient.

16. The method of claim 15 wherein the thermal gradient about the selected area is determined by forcing the thermal image on the image plane to oscillate at a selected frequency and amplitude, performing a lock-in operation on the thermal image at the selected frequency and calculating the thermal gradient from known frequency and amplitude.

17. A method of detecting three dimensional motion of a object in space, comprising the steps of:

heating selected portions of an object to a temperature slightly above ambient;

repeatedly at selected time intervals obtaining images of the heated portions of the object with at least two thermal cameras which are spaced apart combining the images from the at least two thermal cameras to determine three dimensional position of the heated portions with respect to time.

18. A method of monitoring motion of a person comprising the steps of:

warming a plurality of individual selected portions of a body of the person above the temperature of surrounding tissue;

repeatedly at selected time intervals obtaining images of the individual selected portions of the body with at least two thermal cameras which are spaced apart;

combining the images from the at least two thermal cameras to determine three dimensional position of the heated portions with respect to time.

* * * * *